United States Patent [19]

Nobbio

[11] Patent Number: Plant 7,165

[45] Date of Patent: Feb. 20, 1990

[54] CARNATION NAMED LADYCHINERA

[76] Inventor: Giacomo Nobbio, Strada Villetta, 17, San Remo, Italy

[21] Appl. No.: 252,592

[22] Filed: Oct. 3, 1988

[51] Int. Cl.[4] ..... A01H 5/00

[52] U.S. Cl. ..... Plt./71

[58] Field of Search ..... Plt./71

*Primary Examiner*—James R. Feyrer

*Attorney, Agent, or Firm*—Charles W. Rummler

[57] ABSTRACT

A new carnation cultivar particularly distinguished by the uniform light coloration of its very large, double flowers which have exceptional endurance as cut flowers and excellent suitability for shipment, the plant itself being particularly well suited to commercial greenhouse cultivation for the production of cut flowers.

1 Drawing Sheet

BACKGROUND OF THE NEW PLANT

This carnation cultivar originated as a sport of 'Chinera' (U.S. Plant Pat. No. 5,767) being grown at my nursery at Sanremo Italy, for commercial purposes, this new variety being discovered by me during the course of my regular inspection in 1987 of my plants being grown for commercial purposes. It was a somewhat deeper light pink coloration of this sport compared with its parent that caught my attention and accordingly this sport was propagated by means of cuttings through several successive generations to determine that its novel characteristics would hold true from generation to generation. It was thus found that the novel characteristics appeared to be firmly fixed and its homogeneity was assured.

DESCRIPTION OF THE DRAWING

My new carnation cultivar is illustrated by the accompanying full color photographic drawing, which shows the inflorescence of a fully grown plant, the view including buds in several stages of development, as well as a flower in full bloom and specimens of the flower petals, the color shown being as nearly true to that herein specified as is reasonably possible to obtain by means of conventional, professional photographic procedures.

DESCRIPTION OF THE NEW PLANT

The following is a detailed description of my new carnation variety based upon observation of plants grown under conventional greenhouse procedures in 1988, the color designation being according to The R.H.S. Colour Chart published by The Royal Horticultural Society of London, England.

THE PLANT

Origin: Sport.

Parentage: The variety 'Chinera' (U.S. Plant Pat. No. 5,767).

Classification:

*Botanic.*—*Dianthus caryophyllus.*

*Commercial.*—Greenhouse Carnation.

Form: Bush having a total height of seven internodes.

Growth: Upright and vigorous.

Branching: Medium in number. Generally the original stem is pinched at a height of about 10 to 12 cm. from the base after it has reached a height of 30 cm. in order to promote the production of about four or five lateral shoots. The shoots grow rapidly and branch freely. The flower being terminal on each of the branches which may be pinched or pruned according to the desired length of the flower stem.

Foliage:

*Quantity.*—Moderate.

*Leaf size.*—Medium in both length and breadth.

*Leaf shape.*—Linear with entire margins and acuminate apex.

*Texture.*—Smooth.

*Color.*—Green.

THE BUD

Size: Large.

Form: Ovoid immediately before the sepals divide and becoming bell-shaped upon opening.

Sepals:

*Character.*—The sepals are upstanding and remain erect as the flower opens.

Calyx:

*Size.*—Medium.

*Shape.*—Like a truncated cone.

*Aspect.*—Smooth.

*Splitting.*—The calyx does not split.

Peduncle:

*Character.*—Rigid and erect.

THE FLOWER

Blooming habit: Continuous.

Flower size: Very large and double.

Borne: Singly on strong, upright carefully prepared stems.

Shape: Symmetrical and bunched in cupule when in full bloom.

Petalage:

*Number of petals.*—More than eighty.

*Shape.*—Generally fan-shaped with laciniated margin.

*Color.*—Coral Pink, R.H.S. 38-C/D.

*Color distribution.*—Monochrome.

*Texture.*—Soft.

*Appearance.*—Satiny.

*Fragrance.*—Very faint or none.

*Persistence.*—The petals hang on and dry.

*Lasting quality.*—Exceptional as a cut flower.

THE REPRODUCTIVE ORGANS

Androecium: Not present during winter period.

Stamens:

*Number.*—One or two, only in Summer and not in every flower.

*Anthers.*—Size: Normal. Color: Cream.

*Filaments.*—Length: About 1 to 1.5 cm. Color: White.

*Pollen.*—Color: White.

Pistils:

*Number.*—From four to eight.

*Styles.*—Color: Cream, lightly shaded with green.

*Stigmas.*—A smooth surface having a cream color.

Ovary: Long, irregular in shape and ribbed.

This new variety of carnation is distinguished by its relatively dark pink color compared with its parent variety. Otherwise, the flower shape and size is like that of the parent plants being of the double type and having petals that are deeply laciniated to the extent of about 13 mm. As is its parent variety, this new plant is well suited to commercial greenhouse cultivation for the production of cut flowers which have exceptional endurance and good stability for shipment.

I claim:

1. The new and distinct carnation variety, substantially as herein shown and described, characterized by its light pink monochrome flowers of the double type.

* * * * *

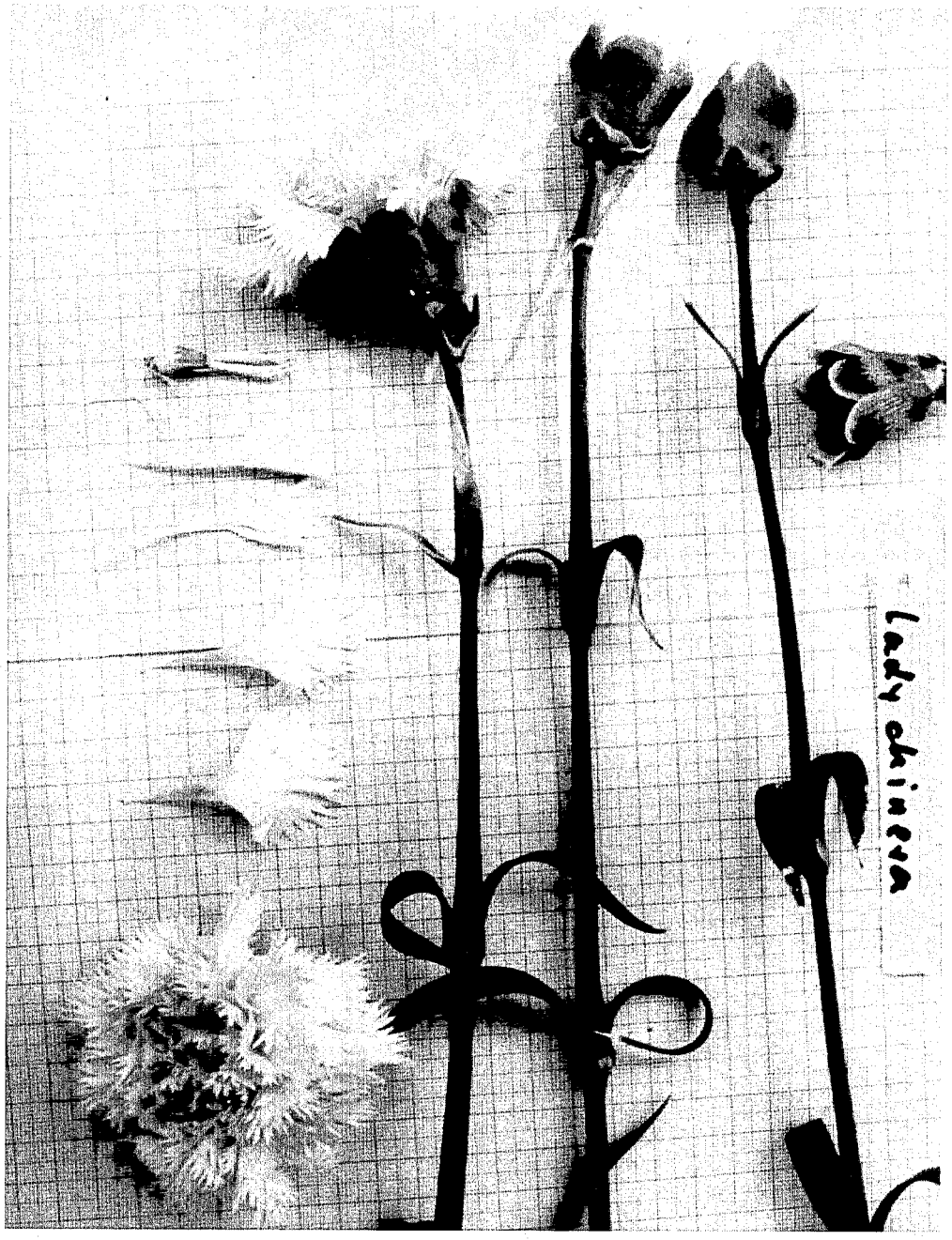
lady chinera